(12) United States Patent
Schwartz et al.

(10) Patent No.: US 8,936,638 B2
(45) Date of Patent: Jan. 20, 2015

(54) CORAL BONE GRAFT SUBSTITUTE

(75) Inventors: Ohad Schwartz, Herzliya (IL); Itzhak Binderman, Tel Aviv (IL)

(73) Assignees: Ramot At Tel-Aviv University Ltd., Tel-Aviv (IL); Corebone Ltd., Misgav (IL)

( * ) Notice: Subject to any disclaimer, the term of this patent is extended or adjusted under 35 U.S.C. 154(b) by 0 days.

(21) Appl. No.: 13/825,466

(22) PCT Filed: Sep. 22, 2011

(86) PCT No.: PCT/IL2011/000751
§ 371 (c)(1),
(2), (4) Date: May 7, 2013

(87) PCT Pub. No.: WO2012/038962
PCT Pub. Date: Mar. 29, 2012

(65) Prior Publication Data
US 2013/0226310 A1     Aug. 29, 2013

Related U.S. Application Data

(60) Provisional application No. 61/385,821, filed on Sep. 23, 2010.

(51) Int. Cl.
*A61F 2/28* (2006.01)
*A61F 2/30* (2006.01)
*A61L 27/36* (2006.01)
*A61L 27/56* (2006.01)

(52) U.S. Cl.
CPC ............... *A61F 2/28* (2013.01); *A61L 27/3604* (2013.01); *A61L 27/365* (2013.01); *A61L 27/56* (2013.01)
USPC ..................... 623/16.11; 623/11.11; 623/23.5; 623/23.51

(58) Field of Classification Search
CPC .......................... A61F 2/28; A61F 2002/2835
USPC ........ 623/11.11, 16.11, 23.5–23.56; 424/93.7
See application file for complete search history.

(56) References Cited

U.S. PATENT DOCUMENTS

| 7,008,450 B2 | 3/2006 | Kim et al. |
| 7,704,561 B2 † | 4/2010 | Mehta |
| 2012/0058152 A1 * | 3/2012 | Garcia de Castro Andrews et al. ............................. 424/400 |

FOREIGN PATENT DOCUMENTS

WO     WO 2009/066283  A2     5/2009

OTHER PUBLICATIONS

Abe, "Factors Controlling Dissolved Silica in Coral Reef Surface Water of Urasoko Bay, Ishigaki Island, Japan," Journal of Oceanography, 2008, vol. 64, pp. 961-967.
Costa et al., "Seasonal and spatial controls on the delivery of excess nutrients to nearshore and offshore coral reefs of Brazil," Journal of Marine Systems, 2006, vol. 60, pp. 63-74.
Cornell et al., "Current Understanding of Osteoconduction in Bone Regeneration," Clinical Orthopaedics and Related Research, 1998, vol. 355S, pp. S267-S273.
Bahar et al., "Influence of Bone-Derived Matrices on Generation of Bone in an Ectopic Rat Model," Journal of Orthopaedic Research, May 2010, pp. 664-670.
Demers et al., "Natural coral exoskeleton as a bone graft substitute: A review," Bio-Medical Materials and Engineering, 2002, vol. 12, pp. 15-35.
Daculsi et al., "Crystal Dissolution of Biological and Ceramic Apatites," Calcified Tissue International, 1989, vol. 45, pp. 95-103.
Guillemin et al., "The use of coral as a bone graft substitute," Journal of Biomedical Materials Research, 1987, vol. 21, pp. 557-567.
Cunin et al, "Experimental Vertebroplasty Using Osteoconductive Granular Material," Spine, 2000, vol. 25, No. 9, pp. 1070-1076.
Arnaud, "Advances in cranioplasty with osteoinductive biomaterials: summary of experimental studies and clinical prospects," Child's Nervous System, 2000, vol. 16, pp. 659-668.
Shors, "Coralline Bone Graft Substitutes," Orthopedic Clinics of North America, Oct. 1999, vol. 30, pp. 599-613.
Le Guéhennec et al, "A Review of Bioceramics and Fibrin Sealant," European Cells and Materials, 2004, vol. 8, pp. 1-11.
Kokubo, "Bioactive glass ceramics: properties and applications," Biomaterials, 1991, vol. 12, pp. 155-163.
Carlisle, "Silicon: A Possible Factor in Bone Calcification," Science, 1970, vol. 167, pp. 279-280.
Place et al., "Complexity in biomaterials for tissue engineering," Nature Materials, 2009, vol. 8, pp. 457-470.
Jugdaohsingh, "Silicon and Bone Health," J Nutr Health Aging, 2007, vol. 11, pp. 99-110.
S.A. Al-Rousan et al., "Heavy metal contents in growth bands of Porites corals: Record of anthropogenic and human developments from the Jordanian Gulf of Aqaba," 54 Marine Pollution Bulletin 1912-22 (2007).†
J.D. Carriquiry et al., "The Ba/Ca record of corals from the Southern Gulf of Mexico: Contributions from land-use changes, fluvial discharge and oil-drilling muds," 60 Marine Pollution Bulletin 1625-30 (2010).†
C.P. David, "Heavy metal concentrations in growth bands of corals: a record of mine tailings input through time," 46 Marine Pollution Bulletin 187-96 (2003).†
F. Maehira et al., "Effects of calcium sources and soluble silicate on bone metabolism and the related gene expression in mice," 25 Nutrition 581-89 (2009).†
Y. Uema et al., "Silicon-rich Coral Sand Improves Bone Metabolism and Bone Mechanical Properties in Mice, "59 J. Japanese Soc'y of Nutritional Food Science 265-70 (2006).†

* cited by examiner
† cited by third party

*Primary Examiner* — Jason-Dennis Stewart
(74) *Attorney, Agent, or Firm* — Oliff PLC

(57) ABSTRACT

This invention provides a method for producing bioactive coral bone graft substitutes and to products obtained thereby.

16 Claims, No Drawings

CORAL BONE GRAFT SUBSTITUTE

FIELD OF THE INVENTION

This invention generally relates to the field of bone substitutes. More particularly, the invention relates to methods for producing bioactive coral bone graft substitutes and to products obtained thereby.

BACKGROUND OF THE INVENTION

Generation of bone is a challenge many scientists in the fields of tissue engineering have been facing with not much success. Bone generation depends, to a great extent, on bioactive scaffolds and on osteoprogenitors. A number of different synthetic calcium based bone graft substitutes (BGS) are currently available for clinical use. Although these materials have demonstrated clinical effectiveness in terms of defect fill, predictability for high rate of success in terms of regeneration has not yet been achieved. Several biomaterials have been developed to fill and reconstruct bone defects: natural coral, bovine porous demineralized bone, human demineralized bone matrix (DBM), bioactive glass ceramics and calcium phosphate ceramics such as hydroxyapatite, β-tricalcium phosphate or biphasic calcium phosphate [1,2,3]. These materials are biocompatible and osteoconductive, guiding bone tissue from the edges toward the center of the defect. Some materials of biological origin, such as bovine bone (xenografts), demineralized bone matrix (DBM) and allogenic bone grafts may have osteoinductive properties. However, biologically-derived organic materials present a risk of an immunological response and disease transfer, and the manufacturer must apply viral inactivation. Although many types of materials are currently available for bone repair, they are being continuously optimized with regard to their chemistry, architecture, and mechanical properties to more closely mimic the properties of bone itself. Among the decisive factors to the success of tissue engineering strategies for bone regeneration is the appropriate design of the scaffold to guide cellular responses toward bone differentiation. The materials used for bone augmentation or repair are measured as being biocompatible, bioactive and able to undergo total degradation without toxic residues. Also, it is expected that over time bone tissue will replace the grafted materials.

The most suitable synthetic bone graft that is currently available to clinicians is osteoconductive or having bone-bonding properties, rather than being bioactive. The general opinion, however, is that these synthetic bone grafts only passively support bone formation and generally do not induce bone formation. Bone regeneration still remains a challenge in tissue engineering; different approaches, based either on bone grafts, or on artificial materials, such as ceramics, hydroxyapatite-based products and polymers, are widely investigated.

In bone replacement, bioactive materials can form intimate bonds with a bone tissue. They are used alone, as carriers for growth factors, as coatings on metallic implants, and as tissue-engineering scaffolds. It has been shown that most of these materials are biocompatible rather than bioactive, namely having no inherent biological activity. In clinical applications of tissue engineered bone regeneration, a material must be identified that can fulfill the pragmatic functions of a scaffold and carrier. Furthermore, the material should facilitate mesenchymal adult stem cells (MCs) differentiation along the osteoblastic pathway. Whether or not the physiology of cells is differently affected by adhesion to these inorganic surfaces is not known; however, adhesion-mediated changes in gene transcription may be responsible for osteogenesis on one scaffold but not on another. Besides the composition of material, another important variable to consider when predicting the eventual fate of the MCs is the interaction between the MCs and their physical properties, such as topography and stiffness.

Natural coral bone graft substitutes (BGS) are derived from the exoskeleton of marine madreporic corals. Natural coral (Porites) consists of a mineral phase, principally calcium carbonate in the structural form of aragonite with impurities, such as Sr, Mg and F ions, and an organic matrix. Researchers first started evaluating corals as potential bone graft substitutes in the early 1970s in animals and in 1979 in humans. The structure of the commonly used coral, Porites, is similar to that of cancellous bone and its initial mechanical properties resemble those of bone. Commercially available coral (Biocoral™) is used as a bone graft material and has been reported to be biocompatible and resorbable [4,5]. This biomaterial is also osteoconductive and resorbable, resulting in the complete regeneration of bone tissue within 6 months, as shown by radiographic follow-up analysis [1,4,5]. Coral has also been used clinically with good results in spinal fusion [5,6], cranial surgery [7] or to fill periodontal defects. Coral-derived material described as coralline HA is also commercially-available (Pro Osteon®, Interpore Cross). It is prepared by hydrothermally converting the original calcium carbonate of the coral Porites in the presence of ammonium phosphate [8]. This hydrothermal process maintains the original interconnected macroporosity of the coral. Coralline HA was identified as a core carbonated hydroxyapatite (CHA) on inner $CaCO_3$ struts. As a result of this heterogeneity, coralline HA dissolves and reacts inconsistently in vivo. Highly porous calcium phosphate ceramics can also be obtained from porous-apatite of lime-encrusted ocean algae (Frios® Algipore®). The manufacturing process retains the pure mineral framework of the algae, leaving an interconnected porous structure and a rough surface. It has been shown that the biomaterial is resorbed slowly and substituted by the host bone [9].

The exoskeleton of these high content calcium carbonate scaffolds has since been shown to be biocompatible, osteoconductive, and biodegradable at variable rates depending on the exoskeleton porosity, the implantation site and the species. Although not osteoinductive or osteogenic, coral grafts act as an adequate carrier for growth factors and allow cell attachment, growth, spreading and differentiation[2,9]. When applied appropriately and when selected to match the resorption rate with the bone formation rate of the implantation site, natural coral exoskeletons have been found to be impressive bone graft substitutes.

Bioactive bone substitutes that have been used as bone replacement materials are based on $SiO_2$ incorporated into CaO and MgO bioceramics, also termed bioglass. Kokubo proposed that Si ions are gradually released from the biomaterial [10]. Carlisle et al. found that Si plays a critical role for generation of bone tissue. The newly formed bone always contains about 0.5% of Si [11].

By itself, pure hydroxyapatite (HA) mineral is a poor bone substitute [12]. Mineral bone substitute that consists of tricalcium phosphate and HA (40:60%) was found to be optimal as a biocompatible biomaterial [13].

U.S. Pat. No. 7,008,450 [14] discloses a method of affecting the coral surface by coating coral with silicium, magnesium and phosphate by a hydrothermic procedure to get a surface of hydroxyapatite with 0.6 wt % of silicium.

REFERENCES

[1] Cornell C N, Lane J M. Current understanding of osteoconduction in bone regeneration. Clin Orthop Relat Res. 1998; S267-73.
[2] Bahar H, Yaffe A, Boskey A, Binderman I. Influence of bone-derived matrices on generation of bone in an ectopic rat model. J Orthop Res. 2010; 28(5):664-70.
[3] Demers C, Hamdy C R, Corsi K, Chellat F, Tabrizian M, Yahia L. Natural coral exoskeleton as a bone graft substitute: a review. Biomed Mater Eng. 2002; 12(1):15-35.
[4] Daculsi G, LeGeros R Z, Mitre D. Crystal dissolution of biological and ceramic apatites. Calcif Tissue Int. 1989; 45(2):95-103.
[5] Guillemin G, Patat J L, Fournie J, Chetail M. The use of coral as a bone graft substitute. Spine (Phila Pa. 1976). 2000; 25(9):1070-6.
[6] Cunin G, Boissonnet H, Petite H, Blanchat C, Guillemin G. Experimental vertebroplasty using osteoconductive granular material. J Biomed Mater Res. 1987; 21(5):557-67.
[7] Arnaud E. Advances in cranioplasty with osteoinductive biomaterials: summary of experimental studies and clinical prospects. Childs Nerv Syst. 2000; 16(10-11):659-68.
[8] Shors E C. Coralline bone graft substitutes. Orthop Clin North Am. 1999; 30(4):599-613
[9] Le Guéhennec L, Layrolle P, Daculsi G. A review of bioceramics and fibrin sealant. Eur Cell Mater. 2004; 8:1-10; discussion 10-1.
[10] Kokubo T., Bioactive glass ceramics: properties and applications. Biomaterials. 1991; 12:155-163
[11] Carlisle E M, Silicon: A possible factor in bone calcification. Science. 1970; vol 167: 279-280.
[12] Bahar et al. Influence of bone-derived matrices on generation of bone in an ectopic rat model. J of Orthop Res. 2010; 28:664-670.
[13] Place et al., Complexity in biomaterials for tissue engineering. Nature Materials; 2009, 8:457-470.
[14] U.S. Pat. No. 7,008,450.

SUMMARY OF THE INVENTION

Coral mineral is composed mainly of calcium carbonate, employed in a modified form as bone graft substitute (BGS) in orthopedics, neurosurgery and dentistry. Modifications made to coral mineral consist mainly of chemical treatments of corals harvested from the sea. Such modifications are limited to the surface of the coral and not evenly distributed within the material.

The inventors of the present invention have developed a method for producing a porous bioactive coral bone graft substitute, the method involving modifying the mineral structure and/or chemistry of the coral (e.g., farmed raised, captive-bred corals), in its habitat (e.g. natural habitat, artificial habitat), during its growth and mineralization. These methods of the invention have the advantage that chemical and structural modifications, carried out during the growth of the coral colony in the habitat, result in the distribution of the added nutrient in the coral tissue and produce coral bone graft substitute which is bioactive.

Thus, in one of its aspects the present invention provides a method for producing a bioactive coral bone graft substitute (BGS), the method comprising growing a coral in a growth medium comprising at least one nutrient, the nutrient being absent from the coral natural habitat or is present in the coral natural habitat at a low concentration (i.e., a concentration lower than that used in accordance with the method of the invention and which is not sufficient to be absorbed in the coral to obtain a nutrient-rich coral); and harvesting the coral to obtain a bioactive BGS.

In another aspect, the present invention discloses a method for enriching a coral with at least one nutrient, said method comprising growing a coral in a growth medium comprising at least one nutrient, the nutrient being absent from the coral natural habitat or is present in the coral natural habitat at a low concentration (i.e., a concentration lower than that used in accordance with the method of the invention and which is not sufficient to be absorbed in the coral to obtain a nutrient-rich coral); and harvesting the coral to obtain a a nutrient-rich coral.

The "growth medium" is an aqueous based medium (either seawater or freshwater), containing the appropriate food (nutrients) required for coral growth and/or propagation, and which is maintained under appropriate conditions required for coral growth, as further disclosed below. In some embodiments, the growth medium is the complete aqueous environment hosting a single coral or one or more coral colonies. Accordingly, the growth medium is maintained under conditions dictated by the colony as a whole, as well as by a condition associated with one or more of the colonies residing therein.

The coral may be grown in its natural habitat, which is continuously treated with pre-determined concentrations of the at least one nutrient. Alternatively, the coral may be grown in an artificial habitat, such as a coral farm in water containing high concentrations of the at least one nutrient. In either habitat, the growth medium may be chemically filtered (e.g., small doses of media are changed frequently) to maintain optimal water clarity. Since the nutritive quality of all foodstuffs degrades with time, the food in the growth medium is substantially fresh food. Frozen foods and opened packages of dry food are discarded regularly and the foods are stored under proper storing conditions as recognized by a person of skill in the art.

As a person of skill in the art would realize, the nutrient-rich corals grown in accordance with the process of the invention, are grown under conditions which are adapted to provide appropriate conditions necessary for normal growth. Such conditions may for example include temperature, irradiance (amount of sunlight), calcium carbonate saturation, turbidity (water clarity), sedimentation, water salinity, pH and nutrients. Accordingly, various other materials (such as calcium hydroxide) in combination with the herein described nutrients can be added to the coral growth medium.

The growth medium may contain calcium (Ca), magnesium (Mg), potassium (K), sodium (Na), phosphate and iron (Fe) ions. When these ions are added into the growth medium the herein described silicium and phosphate based compounds are better incorporated into the whole volume of the coral mineral.

As used herein, the term "nutrient" refers to any compound which, when added to the coral growth medium, is beneficial to the growth of the coral and produces a bioactive BGS as described herein. In some embodiments, the nutrient is a silicium based compound, such compound may be selected from orthosilicic acid (OSA), sodium metasilicate, monomethyltrisilane, calcium silicate ($Ca_2SiO_4$), calcium inosilicate (known as Wollastonite or $CaSiO_3$), choline stabilized orthosilicic acid and $Si(OH)_4$.

The concentration of the at least one nutrient, not typically present in the coral natural habitat, is not toxic to the coral nor does it interact in any way with any of the other nutrients present in the growth medium. Where the nutrient is silicium, the concentration thereof in the coral growth medium is monitored to a range between about 0.1 mg/liter and about 100 mg/liter. In some embodiments, where the nutrient is sodium methasilicate, the concentration thereof in the coral growth medium is monitored to range between about 10 and about 50 ppm. Where the nutrient is an inorganic phosphate (e.g., sodium or potassium salt), the concentration thereof in the coral growth medium is monitored to a range between about 2 and about 5 mM.

In some embodiments, the at least one nutrient is a growth factor capable of inducing coral growth and/or propagation.

In further embodiments, the at least one nutrient is a mixture of two or more nutrients, each being present in the growth medium at a concentration suitable to maintain normal growth of the coral. The various nutrients can be added at different time points during the growth of the coral, depending on various parameters that affect growth of the coral, as described herein (e.g., temperature, irradiance etc). For example, in accordance with the present invention, phosphate, calcium, silicium based compounds and various growth factors can be added separately (at different time points) or in combination to the coral growth medium depending on the specific condition of the coral colony as affected by various factors, such as water flow and light availability; extent of coral bleaching; calcium carbonate deposition/water pH and also the type of the coral.

The coral is grown in the nutrient-rich growth medium for a period of time until the coral reaches maturity or until sufficient nutrient is absorbed by the coral. The addition of nutrients to the coral growth medium is periodically monitored to ensure optimal concentration of the nutrient in the medium over time, where sampling in conducted under conditions which do not negatively affect (e.g., contaminate) the growing corals.

The corals, according to the invention, may be corals that sexually reproduce or that reproduce asexually. Since sexual reproduction of corals only happens once a year, the manner by which the nutrients, as defined herein, are added to the coral growth medium of the sexually reproduced corals depends on the time of the year and on the stage at which the reproducing coral are in. When asexually reproducing corals are used (i.e., coral that are propagated by fragmenting of the coral by breaking pieces away), the manner of the addition of nutrient is similarly adapted to conform the reproduction of the corals, as recognized by a person of skill in the art. Non-limiting examples of corals which may be used in the method of the invention include a Porite coral, Acropora coral or Goniopora coral; a gonochoristic (unisexual) coral or a hermaphroditic coral; a sexually reproducing coral (by spawning) or an asexually reproducing coral; and a perforate or imperforate choral.

In accordance with the present invention, between about 1% and about 8% (wt %) of silicium may be incorporated into the living coral during its growth and mineralization. In some other embodiments, the nutrient is an inorganic phosphate, such as potassium phosphate, sodium phosphate, and others. In some embodiments, the inorganic phosphate is deposited as tricalcium phosphate in the coral mineral, in a range of between about 1% and about 15% (wt %).

Once the coral has been enriched with the at least one nutrient, it is harvested for further treatment and use. As used herein, the term "harvesting" or any lingual variation thereof refers to the removal of coral polyps from the coral colony. The coral polyps may be harvested by any method known in the art.

In some embodiments, the pore size of the nutrient-rich corals grown in accordance with the method of the invention is between 100 and 1,500 microns. In further embodiments, the pore size of the nutrient-rich corals grown in accordance with the method of the invention is between about 200 and between about 600 microns.

The pores, as described herein, are generally connected with each other (e.g. in a three dimensional structure) to enable a free passage of fluid (e.g. body fluid) and in a BGS according to the invention to enable, e.g. the in-growth of new blood vessels through the pores so that new bone can be regenerated.

The harvested polyps may be treated and further manipulated into a bone graft substitute, which is bioactive, as detailed hereinbelow.

The capacity of the BGS to withstand axially directed pushing forces, namely its compressive strength, may be attenuated by modifying certain growth conditions, such as concentration of nutrients, temperature etc. Generally, the compressive strength of the BGS is between about 1.5 and between about 6 Megapascal (MPa). In some embodiments, the compressive strength of the BGS is about 3 and 5 MPa.

In accordance with the present invention, the BGS is characterized by having an interconnected porous architecture with pores ranging in size between about 300 to between about 1,500 microns, high compressive strength, biocompatibility and resorbability. Thus, in accordance with the present invention the bioactive BGS serves as a biocompatible grafting material that can support in vivo bone regeneration and remodeling (i.e., formation of new bone tissue, ingrowth with blood vessels and bone tissue), making it osteoconductive, osteogenic and osteointegrative. The term "bioactive coral bone graft substitute" (or bioactive BGS) thus intends to encompass a coral derived material, e.g. composed primarily of calcium carbonate with small amount of magnesium and other trace minerals such as fluoride, which upon application to bone (in vitro or in vivo) is able to induce the regeneration and/or remodeling thereof. Osteoconductivity refers to the growth of bony tissue into the structure of a bioactive BGS implant/graft, allowing bone cells as well as blood vessels to weave into and through the coral BGS. Osteogenicity refers to the situation when the osteoblasts that are at the site of new bone formation are able to produce minerals to calcify the collagen matrix that forms the substrate for new bone. Osteointegrativity refers to the formation of mineralized tissue forms that are intimately bonded with the BGS material.

The bioactive BGS, in accordance with the present invention, is capable of acting as an adequate carrier for various growth factors and allows cell attachment, growth, spreading and differentiation onto and/or into the BGS structure. In accordance with the present invention, the bioactive BGS is further capable of maintaining proper porous structure to enable in-growth of blood vessels and native bone when the bioactive BGS is used as an implant, as described herein.

In another of its aspects, the invention provides a nutrient-rich coral, comprising a high concentration of at least one nutrient as defined herein. The nutrient rich coral, as defined herein, may be in the form of a particulate material or in the form of blocks.

In yet another one of its aspects, the coral BGS of the invention may be used for filling bone defects in vivo in conjunction with standard methods of internal and external fixation (for example following trauma). The coral BGS of the invention may be used as filler with the advantage that unlike synthetic bone materials or bone allograft, the coral BGS does not activate inflammation or immune responses in the body to the extent that synthetic bone grafts do.

In some embodiments, the implant comprising the coral BGS of the invention is used as a bone graft in a condition selected from fusions of the spine, fusions of the joints in the arms and legs, fractures, gaps in bones caused by trauma or infection, revision joint surgery and oral/maxillofacial surgery. It is noted that in accordance with the present invention the filler comprising the herein defined coral BGS, may be shaped by the surgeon to fit the affected area prior to its implantation at a site where bone growth and/or healing is required In some embodiments, the filer is dental filler. When the filler is used as dental filler it may be used as a prosthetic filler for dental applications or as a dental coating material.

In accordance with the present invention, the coral BGS may be treated with a variety of substances prior to its use in bone healing/growth. Some non-limiting examples of such substances include bone morphogenic protein (BMP) (e.g. BMP-2, BMP-4, and BMP-7), transforming growth beta (TGF-b), platelet-derived growth factor (PDGF), fibroblast growth factor (FGF), etc.

In some embodiment, cells are added to the BGS prior to its implantation as filler at a site where bone growth and/or healing is required. In some embodiments, the cells are mesenchymal stem cells. In other embodiments, the cells are bone marrow cells. When bone marrow cells are introduced, either fresh whole marrow or in vitro expanded populations of bone-marrow cells may be used.

The additional substances may be added in a mixture with the coral BGS (i.e., added to the coral BGS post harvesting, after grinding when the BGS is in particulate form), before or after application of the coral BGS.

In accordance with the present invention, the coral BGS may be seeded onto a support matrix (e.g., when mesenchymal stem cells are used) to induce growth of a replacement repair bone tissue.

In some embodiments, the coral BGS is used in combination with ceramic based bone graft substitutes, such as calcium phosphate, calcium sulfate and bioglass.

In some other embodiments, the coral BGS is used in combination with degradable and nondegradable polymers-based bone graft substitutes such as Cortoss®, OPLA®, Immix®.

In another one of its aspects, the present invention provides a scaffold for use in cell growth and/or propagation, wherein the scaffold comprises a coral BGS of the invention. The scaffold may be used to stimulate bone and cartilage growth, when transplanted into the joints, by stimulating mesenchymal stem cells in the bone marrow to produce new bone and cartilage.

In accordance with the present invention, the herein defined coral BGS and scaffold may be used for transplantation (e.g. subcutaneous) with or without the addition of cells (e.g. fresh marrow).

DETAILED DESCRIPTION OF THE INVENTION

For biomaterials to be used as a substitute material for bone, the biomaterials should be quickly associated with live bone. For this purpose, a bone substitute material is selected to have a porous structure in which pores in size of 100-1,500 microns are three dimensionally connected with each other creating interconnected tunnels similar to human cancellous (spongy) bone. This is required because when the bone substitute is implanted, body fluid (e.g. blood supply) can freely pass through the pores so that a new bone can be generated and ingrow into pores. A natural coral is similar to a human cancellous bone in structure, but comprises calcium carbonate (aragonite or calcite) rather than hydroxyapatatite (HA) and its structure is stronger (3.5-5.8 MPa of coral in comparison to average of 1.4 MPa for human bone).

In the mineral that makes up bones of a human body, some of Ca, P and OH sites in the hydroxyapatite (HA) mineral are substituted with a small amount of other ions. For example, Ca may be substituted by Mg or strontium, P may be substituted by silicium and carbonate, and OH (hydroxyl ions) by fluoride. Substituted ions affect surface charge, surface structure, strength, solubility and bioactivity. Silicon exists as silicate ions, which have a tetrahydral structure. In the coral minerals, some of the Ca, P and O sites (in the coral mineral) may be similarly substituted with a small amount of other ions. In some embodiments, the P sites or carbonate ion sites are substituted with silicate ions.

The present invention provides a bioactive coral bone graft substitute (BGS) that comprises coral mineral enriched by silicate ions (Si) and/or phosphate ions (P). These ions are incorporated into the coral mineral during the coral growth in aquarium by addition of silicate ions (e.g. $Si(OH^-)_4$; $Na_2Si_3O_7$;), under strict controlled conditions. The temperature, pH and ionic strength of the herein described growth medium is strictly controlled. Generally, Silicium may be added to the herein described growth medium as Orthosilicic acid (OSA) (being water soluble at 125 mg/liter) or as monomethyltrisilane (similar to OSA) which is 50% bioavailable to the living coral.

Calcium silicate may be added to a reservoir of calcium carbonate which is dissolved by $CO_2$ ($H_2CO_3$ acid). Wollastonite—a naturally occurring silicium-rich mineral ($CaSiO_3$) may also added and dissolved together with $CaCO_3$ by $H_2CO_3$, in the growth medium. All of the herein described silicium ions sources enrich the coral mineral during its mineralization in vivo and provide the coral mineral with highly bioactive properties (e.g. osteophilicity, osteoconductivity).

Thus, the present invention provides a porous calcium carbonate coral mineral bone substitute biomaterial that (during its growth and its mineralization) incorporates silicium ions, in some embodiments, about 5 wt/% and demonstrates bioactive properties.

Natural coral mineral made of calcium carbonate is biocompatible for bone formation in a rat ectopic bone formation model and is used as starting material. Thus, coral mineral that includes fresh marrow is transplanted subcutaneously in the thoracic region of recipient DA rats.

Another advantage of the herein described BGS is the high mechanical strength and the three dimensionally connected pores (e.g. in size of 100-1,500 um), similar to cancellous bone structure. Enrichment of coral mineral structure and chemistry by silicium ions during the growth and mineralization of the living coral significantly increases the bioactivity of the coral bone substitute to a level of autologous bone transplants (known to be highly bioactive).

The herein described bioactive coral bone graft substitute comprises calcium carbonate (Aragonite) enriched with silicium and phosphate ions. In some embodiments, between about 1 and 8 wt % of silicium is incorporated into the living coral during its growth and mineralization. Phosphate, by binding to calcium, is deposited as tricalcium phosphate in the coral mineral, in the range of 2-15 wt %. Mineralization of the coral occurs at subepithelial spaces that contain glycoproteins that bind calcium which interacts with carbonate, nucleating aragonite mineral. The presence of magnesium triggers mineralization. Among other ions present in sea water and in the herein described growth medium (e.g. in the aquarium), Mg, K, Na and Fe can be found. Because these ions are added to the growth medium, the silicium and phosphate are incorporated into the whole volume of the coral mineral rather than to its surface only. The silicium ions are added to the growth medium as orthosilicic acid (OSA) or wollastonite that contains calcium carbonate. The calcium carbonate and the silicium containing compounds are dissolved by $CO_2$ bubbling into the water in the reservoir, producing $H_2CO_3$.

The herein described silicon containing porous BGS is highly bioactive, and is therefore compatible for use as an artificial bone. Its bioactive properties enable it to bond to newly formed bone creating a connectivity of biomaterial and bone.

Example 1

Silicium is added to the growth medium as calcium silicate to a final concentration of 100 mg/liter. $CO_2$ bubbling in the water produces carbonic acid ($H_2CO_3$) which dissolves the calcium silicate. The dissolved calcium silicate is absorbed by the coral and deposited into the newly formed coral mineral. The coral mineral normally absorbs up to about 5 wt % of silicium. Instead of calcium silicate, wollastonite or orthosilicic acid may be used. The concentrations of calcium silicate, OSA and wollasonite in the growth medium are up to about 200 mg/liter.

The invention claimed is:

1. A method for producing a bioactive coral bone graft substitute (BGS), the method comprising:
   growing coral in an artificial habitat containing a growth medium comprising at least one nutrient, the nutrient being absent from a coral natural habitat or being present in the coral natural habitat at a low concentration, and then
   harvesting the coral to obtain the bioactive coral BGS.

2. The method according to claim 1, wherein the growth medium is seawater or artificial seawater.

3. The method according to claim 2, wherein the growth medium is a complete aqueous environment hosting a single coral or one or more coral colonies.

4. The method according to claim 1, wherein the growth medium is the coral natural habitat being continuously treated with pre-determined concentrations of the at least one nutrient.

5. The method according to claim 1, wherein the artificial habitat is a coral farm.

6. The method according to claim 1, wherein the nutrient is a silicium based compound selected from orthosilicic acid, sodium metasilicate, monomethyltrisilane, calcium silicate ($Ca_2SiO_4$), calcium inosilicate, choline stabilized orthosilicic acid (OSA), and $Si(OH)_4$.

7. The method according to claim 1, wherein the nutrient is an inorganic phosphate selected from potassium phosphate and sodium phosphate.

8. The method of claim 7, wherein the inorganic phosphate is deposited as tricalcium phosphate in a coral mineral in a range of about 1 wt. % to about 15 wt. % based on the total weight of the coral mineral.

9. The method according to claim 1, wherein the at least one nutrient is a mixture of two or more nutrients, each being present in the growth medium at a concentration suitable to maintain normal growth of the coral.

10. The method according to claim 1, wherein the coral is selected from coral families of Porite, Acropora coral, Goniopora coral, gonochoristic coral, hermaphroditic coral; sexually reproducing coral, asexually reproducing coral, perforate and an imperforate choral.

11. The method according to claim 1, wherein the coral has a pore size of 100 to 1,500 microns.

12. A bioactive coral bone graft substitute prepared by the method of claim 1.

13. A method for filling bone defects in vivo, in a subject in need thereof, the method comprising placing onto, in or in the vicinity of a defected bone region a bioactive coral bone graft substitute according to claim 12.

14. The method according to claim 13, wherein the coral bone graft substitute further comprises a substance selected from bone morphogenic protein (BMP), transforming growth beta (TGF-b), platelet-derived growth factor (PDGF), fibroblast growth factor (FGF) and stem cells.

15. The method according to claim 13, wherein bone and/or cartilage growth is stimulated.

16. A method for enriching a coral with at least one nutrient, the method comprising
   growing the coral in a growth medium comprising at least one nutrient, the nutrient being absent from a coral natural habitat or being present in the coral natural habitat at a low concentration, and then
   harvesting the coral to obtain a nutrient-rich coral.

* * * * *